United States Patent
Formanek et al.

(10) Patent No.: US 8,179,527 B2
(45) Date of Patent: May 15, 2012

(54) TERAHERTZ SPECTROMETER

(75) Inventors: Florian Formanek, Tokyo (JP);
Marc-Aurele Brun, Tokyo (JP)

(73) Assignee: Sony Corporation, Tokyo (JP)

( * ) Notice: Subject to any disclaimer, the term of this patent is extended or adjusted under 35 U.S.C. 154(b) by 382 days.

(21) Appl. No.: 12/395,266

(22) Filed: Feb. 27, 2009

(65) Prior Publication Data
US 2009/0225312 A1    Sep. 10, 2009

(30) Foreign Application Priority Data

Mar. 4, 2008  (JP) ................................ 2008-053804

(51) Int. Cl.
*G01J 3/28* (2006.01)
(52) U.S. Cl. ....................................................... 356/326
(58) Field of Classification Search .................... 356/326
See application file for complete search history.

(56) References Cited

U.S. PATENT DOCUMENTS

| 5,703,708 | A | 12/1997 | Das et al. | |
|---|---|---|---|---|
| 7,307,258 | B2 * | 12/2007 | Tao et al. | 250/341.1 |
| 2002/0186370 | A1 * | 12/2002 | Roesner et al. | 356/301 |
| 2005/0100866 | A1 * | 5/2005 | Arnone et al. | 433/215 |
| 2008/0175590 | A1 * | 7/2008 | Perkins et al. | 398/58 |

FOREIGN PATENT DOCUMENTS

| EP | 0723168 A2 | 7/1996 |
|---|---|---|
| JP | 08-005458 | 1/1996 |
| JP | 2008-010637 | 1/2008 |
| WO | 0106915 | 2/2001 |
| WO | 2007-143542 | 12/2007 |

OTHER PUBLICATIONS

Japanese Office Action (JP2008-053804) issued on Dec. 17, 2009.
European Search Report dated Nov. 12, 2010 based on European Patent Appln. No. 09003036.2.

* cited by examiner

*Primary Examiner* — Tarifur Chowdhury
*Assistant Examiner* — Abdullahi Nur
(74) *Attorney, Agent, or Firm* — K&L Gates LLP

(57) ABSTRACT

A terahertz spectrometer includes an optical fiber and an emitter. The optical fiber is branched from a gain fiber constituting an ultra-short pulse oscillator. The emitter generates a terahertz wave from a pulse beam guided from the gain fiber through the optical fiber.

2 Claims, 4 Drawing Sheets

TERAHERTZ SPECTROMETER

CROSS-REFERENCE TO RELATED APPLICATIONS

The present application claims priority to Japanese Patent Application JP2008-053804 filed in the Japanese Patent Office on Mar. 4, 2008, the entire contents of which being incorporated herein by reference.

BACKGROUND

Hitherto known as a technique of generating or detecting terahertz waves is terahertz time-domain spectroscopy (THz-TDS). As known in the art, the terahertz time-domain spectroscopy is suitable for use in imaging samples because the THz-TDS utilizes terahertz waves that define ultra-short pulses, as short as about 100 femtoseconds. Therefore, the terahertz time-domain spectroscopy attracts attention in various technical fields such as industry, medical care, biotechnology, agriculture and security.

In a THz-TDS system, radiation emitted from an ultra-short pulses laser source is split into a pump beam and a probe beam. The pump beam is focused on a terahertz-wave generating element. In the terahertz-wave generating element, a current flow or electrical polarization with a sub-picosecond duration 1 generates a terahertz wave having a field amplitude proportional to the temporal differentiation. The terahertz wave is focused by an optical system on a terahertz-wave detecting element. At this point, the probe beam is applied to the terahertz-wave detecting element. Then, the terahertz-wave detecting element generates a carrier. The carrier is accelerated by the electrical field of the terahertz wave and changed to an electric signal. The time at which the probe beam reaches the terahertz-wave detecting element is delayed, thereby measuring the time waveform the terahertz wave has in the amplitude electric field. The time waveform is Fourier-transformed, thereby determining the spectrum of the terahertz wave.

An apparatus using the terahertz time-domain spectroscopy has been proposed (see, for example, WO 01/06915). In this apparatus, the optical path for the pump beam, which extends from the beam splitter to the terahertz-wave generating element, and the optical path for the probe beam, which extends from the beam splitter to the delay unit are optical fibers.

It has been proposed that some of the spatial optical components of the fiber laser, such as polarizing beamsplitter (PBS), wavelength plate, and collimator lens, should be replaced by optical fibers in order to miniaturize the fiber laser. In the terahertz field, too, there is a strong demand for smaller spectrometers. However, terahertz spectrometers tend to be large because they need optical elements for guiding the pulse beam from the fiber laser to the beam splitter.

SUMMARY

The present disclosure has been made in consideration of the foregoing and proposes a terahertz spectrometer that has a simple configuration and can yet measure samples. The present disclosure relates to a technique of using electromagnetic waves in a frequency band of about $0.1 \times 10^{12}$ THz to $100 \times 10^{12}$ THz.

In view of the above, a terahertz spectrometer according to an aspect of the present invention includes: an optical fiber branched from a gain fiber constituting an ultra-short pulse oscillator; and an emitter configured to generate a terahertz wave from a pulse beam guided from the gain fiber through the optical fiber.

In an embodiment, a pulse beam (pump beam) can be guided from an ultra-short pulse oscillator to an emitter through an optical fiber without propagating in free-space. The terahertz spectrometer can be made smaller than in the case where external optical components are used. As a result, the measuring accuracy can be increased by a decrease in the attenuation of the pulse beam. Thus, this invention can provide a terahertz spectrometer that can measure samples with a simple configuration at higher accuracy than hitherto possible.

Additional features and advantages are described herein, and will be apparent from the following Detailed Description and the figures.

DETAILED DESCRIPTION

An embodiment will be described with reference to the accompanying drawings.

(1) Overall Configuration of the Terahertz Spectrometer

Figure 1:
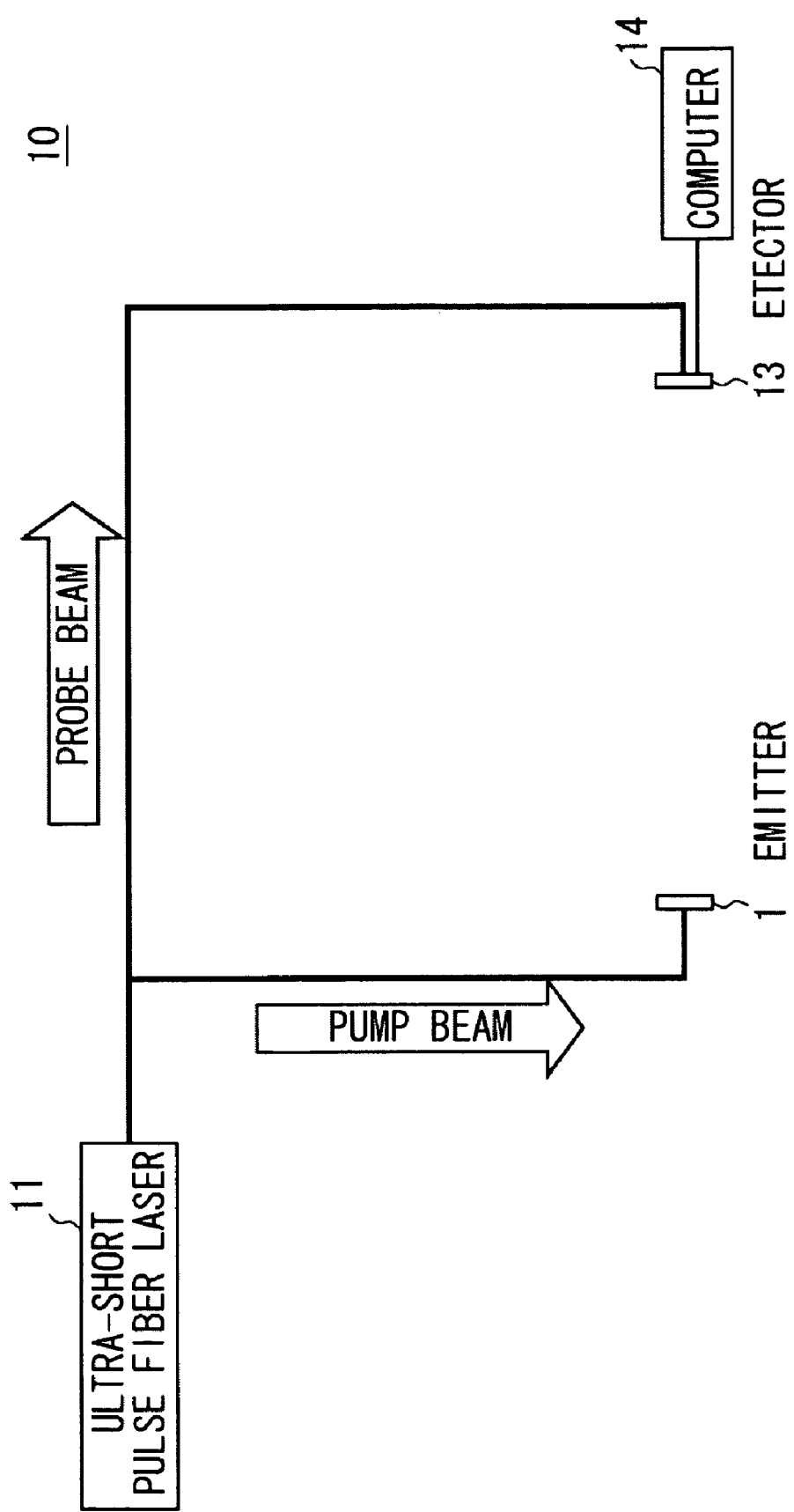
FIG. 1 is a schematic diagram showing the overall configuration of a terahertz spectrometer according to an embodiment.

FIG. 1 shows the overall configuration of a terahertz spectrometer 10 according to an embodiment. This terahertz spectrometer 10 includes an ultra-short pulse fiber laser 11, an emitter 12, a detector 13, and a computer 14.

The ultra-short pulse fiber laser 11 emits a pulse beam having, for example, a pulse width of about 100 fs and a central wavelength of about 800 nm. The ultra-short pulse fiber laser 11 is advantageous over the solid-state titanium-sapphire laser, because it requires no cooling, is cheap, small in size and emits pulses at high efficiency.

The pulse beam emitted from the ultra-short pulse fiber laser 11 is split into a pump beam and a probe beam. The pump beam is guided to the emitter 12. The probe beam is time-delayed with respect to the pump beam and then guided to the detector 13.

The emitter 12 generates a terahertz wave that has an electric field amplitude proportional to the temporal differentiation of the pump beam. In particular, the emitter 12 is, for example, a photoconductive antenna or a nonlinear optical crystal film made of ZnTe or the like. The photoconductive antenna includes a photoconductive film of Si, Ge, GaAs or the like, electrodes for accelerating free electrons energized by the photoconductive film, and a voltage-applying unit for applying a bias voltage to the electrodes.

The detector 13 detects the terahertz wave emitted from the emitter 12 and coming from a sample SPL (either passed through, or reflected by, the sample). That is, the detector 13 generates an electric field equivalent to the terahertz wave coming from the sample SPL. If the probe beam delayed with respect to the pump beam is applied at this point, the detector 13 generates a signal representing the time waveform of the electric-field intensity of the terahertz wave. The detector 13 is, for example, a photoconductive antenna, a nonlinear optical crystal film, or the like.

The computer 14 acquires a signal the detector 13 outputs while a sample SPL to be a measuring object, remains at a prescribed position, and a signal the detector 13 outputs while a sample SPL to be a measuring reference, remains at the prescribed position. The computer 14 extracts the amplitude data and phase data about the terahertz wave, from each of these signals. Based on the difference between the amplitude data items and the difference between the phase data items, the computer 14 acquires information about the sample SPL, i.e., object to be measured. Since the computer 14 can acquire the amplitude data and the phase data at the same time, the terahertz spectrometer 10 is advantageous in terms of measuring accuracy over the Fourier spectroscopy that uses far-infrared beams.

(2) Configuration of the Waveguide

The terahertz spectrometer 10 has a waveguide that extends from the ultra-short pulse fiber laser 11 to the emitter 12 and detector 13 and that is constituted by optical fibers.

Figure 2:
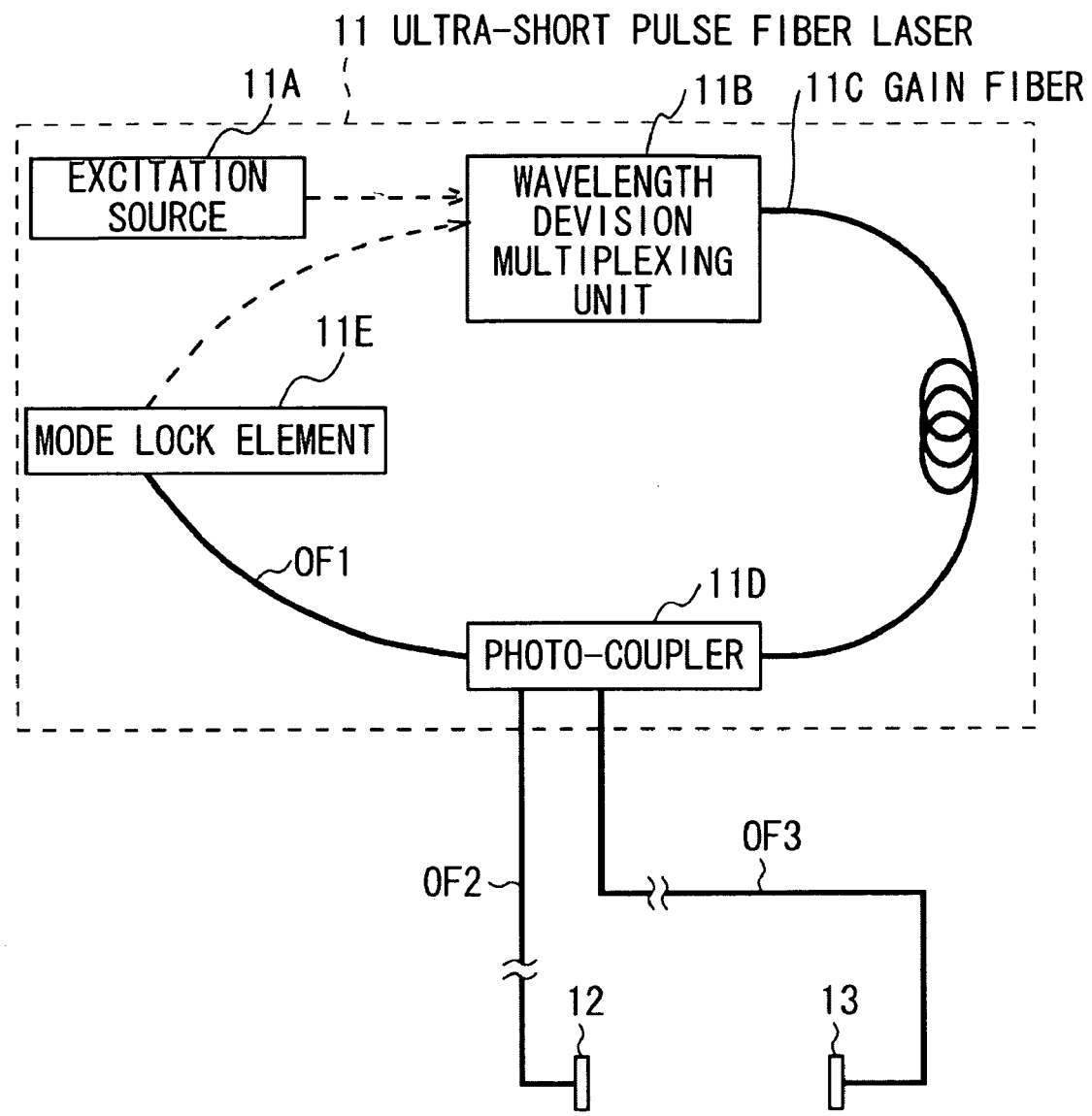
FIG. 2 is a schematic diagram showing an exemplary configuration of a waveguide.

FIG. 2 shows an exemplary configuration of the waveguide. In the ultra-short pulse fiber laser 11 shown in FIG. 2, an excitation source 11A is connected by a wavelength division multiplexing unit 11B to a gain fiber 11C that contains rare earth element such as erbium (Er), and a photo-coupler 11D is connected at input port to the end of the gain fiber 11C.

An optical fiber OF1 is connected, at one end, to the first output port of the photo-coupler 11D, and at the other end, to a mode lock element 11E. The mode lock element 11E generates a pulse beam that is synchronized with the vertical mode of a transmitter and has a function of stabilizing the mode synchronization.

An optical fiber OF2 is connected, at one end, to the second output port of the photo-coupler 11D, and at the other end, to the emitter 12. Thus, the pulse beam output from the gain fiber 11C is branched in the photo-coupler 11D and applied directly to the optical fiber OF2. The optical fiber OF2 guides the pulse beam to the emitter 12.

In the terahertz spectrometer 10, the pulse beam output from the gain fiber 11C to the emitter 12 can therefore be prevented from propagating in a free space.

An optical fiber OF3 is connected, at one end, to the third output port of the photo-coupler 11D, and at the other end, to the detector 13. Thus, the pulse beam output from the gain fiber 11C is branched in the photo-coupler 11D and introduced directly into the optical fiber OF3. The optical fiber OF3 guides the pulse beam to the detector 13.

In the terahertz spectrometer 10, the pulse beam output from the gain fiber 11C to the detector 13 can therefore be prevented from propagating in the free space.

Various types of photo-connectors CN are available, such as SC type, FC type, MU type, FC type and SMA type. Photo-connectors of any type adapted to the shape of fibers used are selected and used. The photo-coupler 11D may be a fused coupler in which optical fibers are fused and connected to have a tapered shape. In this case, the pulse beam output from the gain fiber 11C can be transmitted to the optical fibers OF2 and OF3 at the same time. As a result, the probe beam can be easily adjusted in terms of time with respect to the pump beam.

As known in the art, optical fibers have characteristics of dispersing pulse beams, because their refractive indices change with the wavelength of the input pulse beam. The dispersion of the pulse beam is compensated for by a dispersion compensation unit constituted by an optical system composed of a prism, a grating, a chirped mirror, and the like.

In the terahertz spectrometer 10 according to the embodiment, the dispersion of the pulse beam is compensated for, not by a dispersion compensation unit constituted by an optical system, but by the optical fibers OF2 and OF3. The optical fibers OF2 and OF3 include a plurality of optical fibers that exhibit different in beam-dispersing characteristic in a prescribed band. The optical fibers OF2 and OF3 can therefore compensate for the dispersion of the pulse beam output from the gain fiber 11C.

Figure 3:
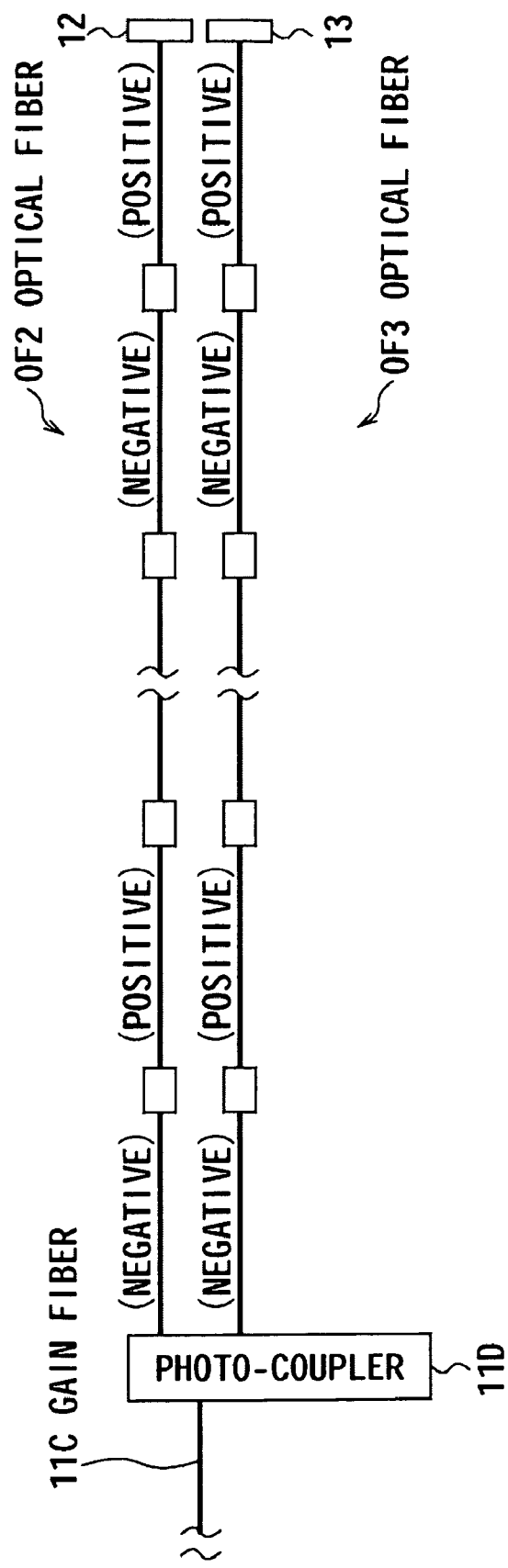
FIG. 3 is a schematic diagram explaining the dispersion compensation achieved by connecting optical fibers of different characteristics.

As FIG. 3 concretely shows, optical fibers exhibiting a positive group velocity dispersion in the above-mentioned prescribed band (solid lines marked as "positive" in FIG. 3) and optical fibers exhibiting a negative group velocity dispersion in the prescribed band (solid lines marked as "negative" in FIG. 3) are alternately arranged and coupled with an optical connector (indicated by rectangles in FIG. 3), thus forming the optical fibers OF2 and OF3. Note that the "prescribed band" is based on the central wavelength of the input pulse beam output from the gain fiber 11C in the ultra-short pulse fiber laser 11. At the input and output ends of each optical fiber thus made (OF2 or OF3), the pulse beam has the same pulse width.

The optical fibers exhibiting a positive group velocity dispersion and the optical fibers exhibiting a negative group velocity dispersion have the same length and are alternately arranged and coupled together, providing the optical fibers OF2 and OF3. This invention is not limited to this configuration. These optical fibers may be coupled together in any other manners, in accordance with the characteristics of the fiber materials used, the length of fibers and the dispersion temperature, so long as the optical fibers OF2 and OF3 compensate for the dispersion of the pulse beam.

Thus, in the terahertz spectrometer 10, a plurality of optical fibers different in dispersion characteristics are coupled, compensating for the dispersion. Therefore, any dispersion compensation unit that is physically independent need not be used.

(3) Configuration of the Time Adjustment Unit

In the terahertz spectrometer 10 according to this embodiment, the time at which the probe beam reaches the detector 13 is delayed not by using a time delay unit having an external optical element such as a retro-reflector, but by applying a temperature load to the optical fiber OF3.

Figure 4:
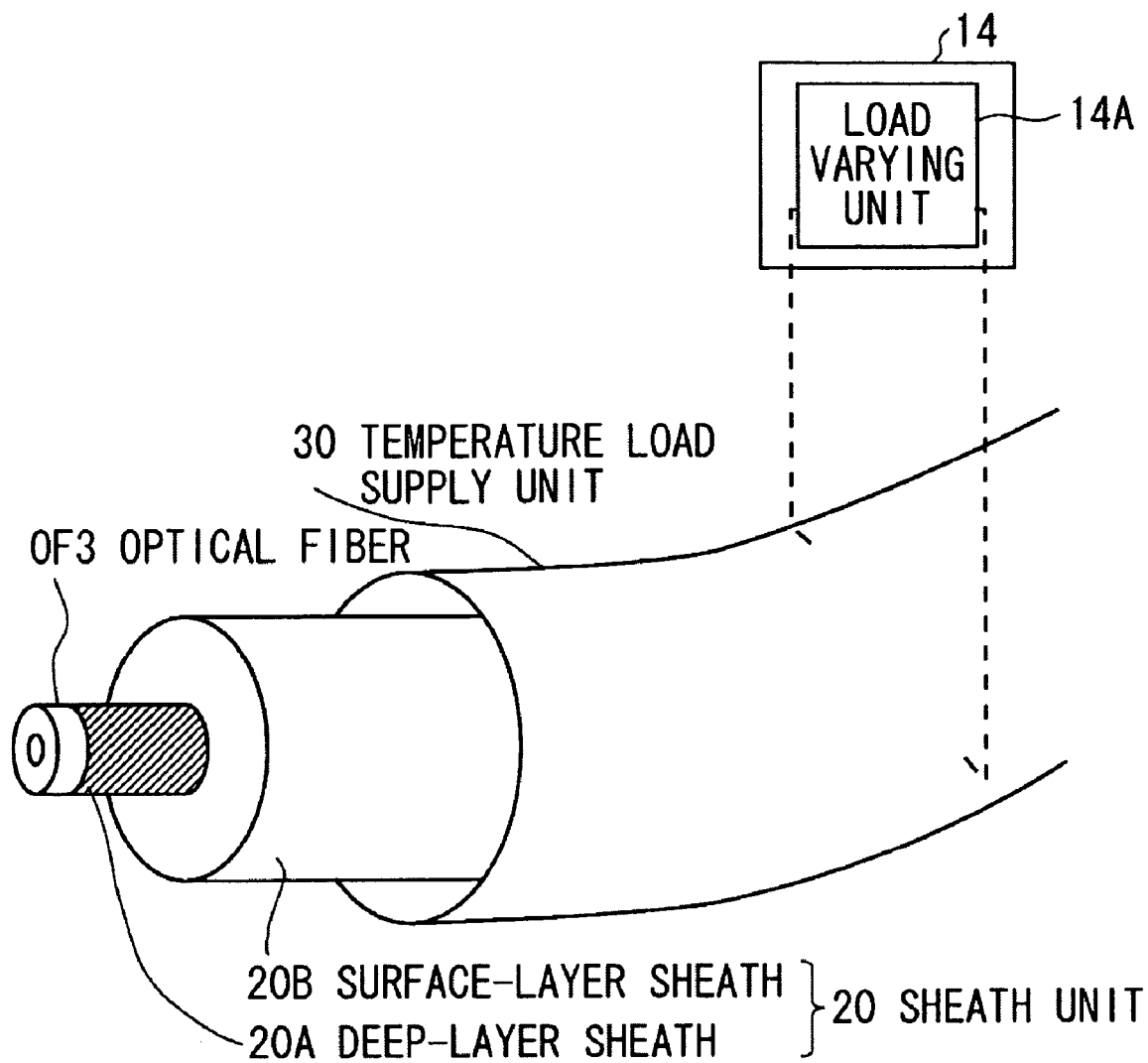
FIG. 4 is a schematic diagram explaining how to adjust the time delay by varying the temperature of an optical fiber.

More specifically, as FIG. 4 concretely shows, the optical fiber OF3 is cover with a sheath unit 20. The sheath unit 20 is composed of a deep-layer sheath 20A and a surface-layer sheath 20B mounted on the deep-layer sheath 20A. The deep-layer sheath 20A is made of plastic or the like, and the surface-layer sheath 20B is made of nylon or the like. Made of these materials, the deep-layer sheath 20A and surface-layer sheath 20B impart mechanical strength and water resistance to the optical fiber OF3. The surface-layer sheath 20B of the sheath unit 20 is covered, in part or entirety, with a temperature load supply unit 30. The temperature load supply unit 30 applies a temperature load set by the load varying unit 14A incorporated in the computer 14. The optical fiber OF3 is thereby maintained at a temperature lower than the optical fiber OF2.

In the terahertz spectrometer 10, the optical fiber OF3 is coupled to compensate for the dispersion at the constant temperature maintained by the temperature load supply unit 30. Thus, the temperature load supply unit 30 functions as a time delay unit. The pulse beam (probe beam) distributed from the photo-coupler 11D to the optical fiber OF3 therefore reaches the detector 13, delayed with respect to the pulse beam (pump beam) distributed from the photo-coupler 11D to the optical fiber OF2.

For the sake of convenience, a single-mode optical fiber is shown in FIG. 4. Nonetheless, a multi-mode fiber can be adjusted in time delay, in the same way as the single-mode optical fiber is adjusted in time delay.

As described above, the time at which the probe beam reaches the detector 13 is delayed by applying a temperature load to the optical fiber OF3. Therefore, any independent time delay unit that is physically independent need not be used.

(4) Operation and Effect

In the terahertz spectrometer 10 so configured as described above, the optical fiber OF2 is coupled by the photo-coupler 11D to the gain fiber 11C provided in the ultra-short pulse fiber laser 11. The pulse beam (pump beam) output from the gain fiber 11C through the optical fiber OF2 is guided to the emitter 12 (FIG. 2).

In the terahertz spectrometer 10, the pulse beam (pump beam) can thus be introduced into the optical fiber OF2 through the ultra-short pulse fiber laser 11, without using an optical lens. The terahertz spectrometer 10 can therefore be smaller than in the case an optical lens is used. In addition, the pulse beam output from the ultra-short pulse fiber laser 11 to the emitter 12 can be prevented from propagating in a free space. As a result, the measuring accuracy can be increased by a decrease in the attenuation of the pulse beam.

In the present embodiment, the optical fiber OF2 is composed of a plurality of optical fibers exhibiting different in dispersing characteristics in a prescribed frequency band and coupled to one another, so that the dispersion of the pulse beam output from the gain fiber 11C may be compensated for (FIG. 3).

The terahertz spectrometer 10 can therefore accomplish the compensation of dispersion, without using a dispersion compensation unit composed of external optical elements. The terahertz spectrometer 10 can be smaller than in the case where a dispersion compensation unit is used. In addition, the maintenance cost can be greatly reduced than in the case where a dispersion compensation unit is used. Moreover, the compensation of dispersion can be easily adjusted as needed when the central wavelength of the laser is changed.

Further, in the terahertz spectrometer 10 according to this embodiment, the optical fiber OF3 is coupled directly to the photo-coupler 11D and guides the pulse beam (probe beam) output from the gain fiber 11C to the detector 13 through the optical fiber OF3 (FIG. 2). The terahertz spectrometer 10 has a time adjustment unit (i.e., temperature load supply unit 30 and load varying unit 14A) that applies a temperature load to a part or entirety of the optical fiber OF3 so that the optical fiber OF 3 may remain at a lower temperature than the optical fiber OF2 (FIG. 4).

Therefore, in the terahertz spectrometer 10, the pulse beam (probe beam) can be introduced into the optical fiber OF3 from the ultra-short pulse fiber laser 11, without using an optical lens and can delay the time at which the pulse beam (probe beam) reaches the detector 13, without using an optical lens such as a retro-reflector lens. The terahertz spectrometer 10 can therefore be much smaller than in the case such an optical lens is used. In addition, the pulse beam output can be prevented from propagating in a free space extending from the ultra-short pulse fiber laser 11 to the detector 13. As a result, the measuring accuracy can be increased by a decrease in the attenuation of the pulse beam.

The embodiment can realize a terahertz spectrometer 10 that can be small because the waveguides, one extending from the ultra-short pulse fiber laser 11 to the emitter 12 and the other extending from the ultra-short pulse fiber laser 11 to the detector 13, are optical fibers.

(5) Other Embodiments

In the embodiment described above, the optical fiber OF3 is branched directly from the gain fiber 11C. The present invention is not limited to this, nevertheless. Instead, the optical fiber OF3 may be branched from the optical fiber OF2. For example, a photo-coupler (or a splitter) may be provided on the waveguide of the optical fiber OF2. In this case, the same advantage can be attained as in the case where the optical fiber OF3 is branched directly from the gain fiber 11C.

In the embodiment described above, the temperature load supply unit 30 covers the sheath unit 20 that in turn covers the optical fiber OF3. This invention is not limited to this. Instead, the temperature load supply unit 30 covers the deep-layer sheath 20A of the sheath unit 20. Alternatively, the temperature load supply unit 30 may directly cover the optical fiber OF3. In this case, the sheath unit 20 can be dispensed with, in part or in entirety. This can render the terahertz spectrometer 10 further smaller.

As described above, the position where the temperature load is applied is the optical fiber OF3. Instead, the temperature load may be applied to the optical fiber OF2. In this case, the temperature load is one that has been set by the load varying unit 14A incorporated in the computer 14 and keeps the optical fiber OF3 at high a temperature. Thus, the same advantage is achieved as in the embodiment described above. That is, if the time at which the pulse beam reaches the detector 13 after passing through a waveguide is delayed with respect to the time at which the beam reaches the emitter 12 from the photo-coupler 11D (i.e., photo-coupler provided on the waveguide of the optical fiber OF2), the position of applying the temperature load can be changed, as needed. The load may be applied to one or both of the waveguides.

The temperature is applied as the load in the embodiment described above. Instead, any other type of load, such as pressure, electric field or commercial fiber delay system may be applied.

In the embodiment described above, the optical fiber to be applied with a load is applied with a load so that it may remain in a "unique" loaded state different from the state in which any other optical fiber to be not applied with a load. This invention is not limited to this, nevertheless. The load may be switched so that the optical fiber may be loaded in "selected" one of various states. If this is the case, the time at which the pulse beam reaches the detector 13 can be switched. As a result, the measuring accuracy can be increased.

In the embodiment described above, the ultra-short pulse fiber laser 11 shown in FIG. 2 is used as an ultra-short pulse oscillator. Any one of the other various ultra-short pulse oscillators can be used instead.

The present invention can be utilized in various technical fields such as industry, medical care, biotechnology, agriculture, security, data communication and electronics.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A terahertz spectrometer comprising:
a first optical fiber branched from a gain fiber constituting an ultra-short pulse oscillator;
an emitter configured to generate a first terahertz wave from a pulse beam guided from the gain fiber through the first optical fiber
a second optical fiber branched from the gain fiber or the first optical fiber;
a detector configured to detect a second terahertz wave by using the pulse beam guided from the gain fiber through the second optical fiber; and
a time adjustment unit configured to apply a load to the first optical fiber or the second optical fiber to be applied with a load so as to maintain the first optical fiber or the second optical fiber in a loaded state different from the state of the first optical fiber or the second optical fiber to be not applied with a load and ultimately to delay the time at which the pulse beam reaches the detector, wherein the first optical fiber or the second optical fiber to which the load is applied is composed of a plurality of optical fibers exhibiting different dispersion characteristics in a prescribed band based on a central frequency of the pulse beam and in a loaded state maintained by the time adjustment unit, and is configured to cancel pulse width dispersion of the pulse beam output from the gain fiber.

2. The terahertz spectrometer of claim 1, wherein the time adjustment unit applies a load to maintain selected one of the loaded states, which is different from the states not selected, so as to delay the time at which the pulse beam reaches the detector.

* * * * *